United States Patent
Rossigneux (10) Patent No.: US 7,654,161 B2
(45) Date of Patent: Feb. 2, 2010

(54) METHOD AND DEVICE OF INSPECTION OF A ROLLED BAND

(75) Inventor: Bernard Rossigneux, Montbrison (FR)

(73) Assignee: Siemens VAI Metals Technologies SAS, Saint Chamond (FR)

( * ) Notice: Subject to any disclaimer, the term of this patent is extended or adjusted under 35 U.S.C. 154(b) by 433 days.

(21) Appl. No.: 11/667,354

(22) PCT Filed: Nov. 8, 2005

(86) PCT No.: PCT/FR2005/050936

§ 371 (c)(1),
(2), (4) Date: May 9, 2007

(87) PCT Pub. No.: WO2006/051239

PCT Pub. Date: May 18, 2006

(65) Prior Publication Data

US 2007/0295881 A1 Dec. 27, 2007

(30) Foreign Application Priority Data

Nov. 10, 2004 (FR) .................................. 04 52595

(51) Int. Cl.
*G01M 19/00* (2006.01)
(52) U.S. Cl. .................................................. 73/865.8
(58) Field of Classification Search .................. 73/799, 73/865.8
See application file for complete search history.

(56) References Cited

U.S. PATENT DOCUMENTS 3,125,229 A * 3/1964 Mulquin et al. ............ 271/10.1

2004/0174518 A1 * 9/2004 Naiki et al. .............. 356/237.2

FOREIGN PATENT DOCUMENTS

| FR | 2710863 A1 | * | 4/1995 |
| JP | 57-94417 A | | 6/1982 |
| JP | 59-113916 A | | 6/1984 |
| JP | 5-223728 A | | 8/1993 |
| JP | 05223728 A | * | 8/1993 |
| JP | 06304655 A | * | 11/1994 |

* cited by examiner

*Primary Examiner*—Hezron Williams
*Assistant Examiner*—Tamiko D Bellamy
(74) *Attorney, Agent, or Firm*—Laurence A. Greenberg; Werner H. Stemer; Ralph E. Locher

(57) ABSTRACT

The invention relates to a method and a device of inspection of a rolled band, wherein a band sample (M) is inspected on a first face then turned over for the inspection of a second face.

According to the invention, by running parallel to its longitudinal axis, the band sample (M) is brought between two spaced apart grips (6, 6') (7, 7') which are clamped respectively on each transversal end (M1, M2) of the sample (M), both grips (6, 6') (7, 7') are spaced apart longitudinally from one another so as to stretch the sample for visual inspection of a first face, then the sample is turned over, by simultaneous rotation of both grips (6, 6') (7, 7') around the longitudinal axis O, while holding the tension applied, so as to proceed to the inspection of the second face, such tension being sufficient to conduct the inspection without the sample contacting a table.

The invention enables, in particular, the inspection of a band at the exit of a continuous rolling line.

22 Claims, 6 Drawing Sheets

METHOD AND DEVICE OF INSPECTION OF A ROLLED BAND

CROSS-REFERENCE TO RELATED APPLICATION

This application is a National Stage entry of International Application No. PCT/FR2005/050936, filed Nov. 8, 2005, the entire specification claims and drawings of which are incorporated herewith by reference.

The invention relates to a method and a device of inspection of a rolled strip, in particular, a rolled metal band.

When rolling a band-type product such as a sheet metal, either face of the product may be marked detrimentally, for instance by the contact of the rolling cylinders, and such marking is repeated periodically during the rolling operation and may be found throughout the coil after the winding of the band. It is therefore necessary, in order to detect possible geometrical defects of the product, to inspect periodically the sheets exiting a rolling mill. To do so, it has been suggested for instance, to use devices of the type including an unwinder/winder associated with an inspection table. A coil inspected is extracted from the usual conveyor so as to be placed on said unwinder which enables to unwind, on the table, a certain length of band for visual inspection. Such devices are heavy and costly and enable to inspect only one face of the band. Moreover, they involve a particular installation since the coil to be inspected must be extracted from the production line and then insert it back into it.

It has also be suggested to use on-line devices enabling to check a certain length of the band cut previously and forming a band sample which may be laid on an inspection table, and then turned over to inspect the other face.

The document JP-A-59113916, for instance, discloses an inspection facility of such type including two spaced apart inspection tables, each comprising a conveyor belt, between which is placed a turning-over device, optionally in two portions, including two superimposed conveyor belts, which are arranged on both sides of a running plane of the metal band and mounted on one or two rotary chassis each including two circular platens which may revolve round a longitudinal axis running through the running plane of the band. A plate of a certain length is brought, first of all, on the first conveyor belt forming an inspection table of its upper face, then is transferred into the turning-over device, so as to be held between both superimposed conveyor belts. After rotation around the longitudinal axis and turning the plate over, the latter is transferred on the conveyor belt forming a second table, situated downstream, for the inspection of the second face. To suit the length of the plate to be examined, the turning-over device has two successive chassis of various lengths which may operate separately or simultaneously.

Such an installation, including a whole set of conveyor belts, is rather complex and cumbersome.

On the other hand, visual inspection techniques have been used until now, for instance under a certain light, but it has been suggested to use a so-called 'honing' technique which consists in rubbing a stone over the face of the band laid on the table, in order to expose the possible defects. Such a technique can be used on a small sample of the band, the turning-over being conducted manually, but it is often preferred to carry out the inspection over a greater length, for instance 10 to 15 meters, in order to locate the defects appearing, periodically, during the rolling operation and may have different causes. To this end, it is possible to take, from the band, a sample of desired length, but if this sample is laid on a table to conduct the honing on the upper face, the lower face may be marked by contact with the table and, after turning over, it is difficult to know whether the defects which may have been located are ascribable to the rolling or to the honing operation itself, such defects being of the artifact type.

The invention relates to a method and a device enabling to solve such problems, while preventing, in particular, the stress of the inspection means from damaging the face which has not been inspected yet.

On the other hand, the invention may adapt different types of installation readily. Indeed, the turning-over device which is relatively little cumbersome can be placed at the outlet of a continuous rolling installation, downstream of the winders but, the method according to the invention also enables the inspection, conventionally, of a coil taken from the production line and placed on an unwinder.

The invention relates therefore to, generally, the inspection of a rolled band from which is taken a band sample which is inspected first on a first face, and then turned over for inspection of a second face.

According to the invention, by running, parallel to its longitudinal axis, the band sample, the latter is brought between two spaced apart grips which are clamped respectively on each transversal end of the sample, then are spaced apart longitudinally from one another so as to stretch the sample for a visual inspection of a first face. The sample is then turned over by simultaneous rotation of both grips around the longitudinal axis while keeping the tension applied, so as to proceed to the inspection of the second face.

Thus, in case when the inspection is conducted by honing, by spacing apart longitudinally both clamping grips, the band sample can be stretched sufficiently so as to conduct the honing on the upper face, without application of the opposite face onto a table, the sample being then turned over while being held under tension, for the inspection by honing of the second face.

In a first embodiment, the band sample is laid, first of all, on a table situated between both spaced apart grips which are clamped respectively to the two ends of the sample and are then spaced apart longitudinally from one another so as to stretch the sample, the table being then withdrawn before carrying out the inspection first of all on a first face then, after turning over, on the second face.

In another embodiment, the band wound in a coil is laid on an unwinder associated with means for controlling the unwinding of the band along a longitudinal direction and shearing means. In such a case, the unwound band is first shorn to provide the band sample with an upstream end which runs successively between the two open grips, respectively a first grip carried by a rotary platen centred on a longitudinal unwinding axis and a second grip carried by a carriage mounted slidingly longitudinally and situated downstream of the first grip. Then the second grip is clamped on said upstream end and the carriage is moved longitudinally downwards to control the unwinding of the band, and to be fastened, with said second grip, on a second rotary platen spaced apart longitudinally from the first platen and centred on a longitudinal axis. The first grip is then clamped on the band and the latter is shorn to provide a downstream end of the band sample, which is thus held in stretched condition between the two grips and can be inspected successively on a first face, then on a second face after turning over by simultaneous rotation of the two platens around their axis, while holding the tension applied.

The invention also covers a device for the implementation of the method, including two spaced apart clamping grips, carried respectively by two platens mounted rotatably around the same longitudinal axis, means for stretching the sample by spacing apart the two grips with respect to one another, after clamping each of them on the corresponding end of the sample for holding it along an inspection plane, and means for controlling the simultaneous rotation, around the horizontal axis, of the two platens with the grips, for turning the sample over while holding the tension applied thereto by spacing apart both grips.

To this end, each rotary platen includes a chassis in the form of a disk, delineated by a circular rim centred on the rotational longitudinal axis and fitted with a rectangular central scalloping wherein are mounted two clamping jaws, respectively a fixed jaw having a planar clamping face situated substantially at the level of the rotational axis, and a mobile jaw including a beam having a planar clamping face parallel to the clamping face of the fixed jaw, and mounted slidingly on the chassis of the platen, perpendicular to said planar faces, and a means for moving the jaws toward one another for clamping and releasing said planar faces.

Particularly advantageously, the two rotary platens are mounted respectively in two supporting stands, having the form of a frame, spaced apart from one another and centred on a vertical medial plane running through the rotational axis. Each stand is carrying at least two rollers spaced apart symmetrically on both sides of the medial plane, on which rollers the rotary platen lies by a lower portion of the circular rim, each roller revolving around an axis parallel to the axis of the rim and synchronised means for controlling the simultaneous rotation, around their axis, of both platens, for turning over the sample clamped between the two pairs of cheeks.

In a first embodiment of the invention, the device includes a means for adjusting the longitudinal spacing between the two rotary platens for stretching the band sample after clamping the jaws. To this end, one of the platens is carried by a fixed stand and the other platen is carried by a mobile stand mounted on a fixed support so as to slide parallel to the rotational longitudinal axis of both platens, said fixed support carrying a means for controlling the sliding of the mobile stand for stretching the band sample after clamping of the grips.

Preferably, in that case, the device includes a table mobile vertically, extending between the two rotary platens and having a planar upper face parallel to the rotational longitudinal axis, and means for a vertical displacement of the table between a raised position, where its upper face lies substantially at the clamping jaws, and a lowered position.

The inspection device according to the invention applies in particular to a rolling installation including successively, along a rolling plane, at least one roll stand, shears and a device for winding the band into a coil.

In such a case, the installation includes, downstream of the shears, switching means having two positions, respectively a first position for guiding the band towards means for winding the band into a coil and a second guiding position, towards the inspection device, for a band sample taken from the band by successive shearing of two ends spaced apart by the required distance.

Advantageously, the conveying means of the band sample between the grips are arranged so as to determine, after cutting the band sample, continuous displacement of the band sample parallel to itself, up to an inspection position between the two rotary platens.

To this end, the conveying means of the band sample include a supporting table having a planar upper face extending, in a pick-up position by the grips, in the clamping plane running through the rotational axis of the two platens and displacement means of the band sample, parallel to itself, from the shears to the supporting table.

In another embodiment, the invention applies to the inspection of a band wound into a coil and placed on an unwinder associated with shears. In such a case, the device still includes two grips for clamping the band situated after one another along the longitudinal unwinding direction, respectively a first grip carried by a first platen situated downstream of the shearing means, in the unwinding direction, and a second grip carried by a carriage mounted slidingly, parallel to the longitudinal unwinding direction, between a first laying and pick-up position of the band, situated immediately downstream of the first grip, and an inspection position for which the carriage for supporting the second grip is fastened on a second rotary platen, spaced apart longitudinally downwards relative to the first rotary platen, and centred on the same longitudinal axis, the second grip being first clamped on an upstream end of the band moving together with the carriage up to the second platen and the band sample being then taken by shearing of its downstream end on which is clamped the first grip. After stretching the band sample, a first face is inspected, then the second face is inspected, after the simultaneous rotation of both grips, while holding the tension applied.

For stretching the band sample, at least one of the grips includes, on the one hand, two clamping cheeks, mounted respectively on two supporting beams movable relative to one another between a spaced apart position and a clamping position of the cheeks and two rolls mounted respectively on the two beams beside the corresponding cheek, at least one of the rolls being offset vertically by a resilient means, so that the corresponding end of the sample is gripped between said offset roll and the other roll before clamping both cheeks, after compressing said resilient means.

The invention also covers other advantageous arrangements which will appear in the following description of certain particular embodiments, given by way of non-limiting example and represented on the appended drawings.

Figure 1:
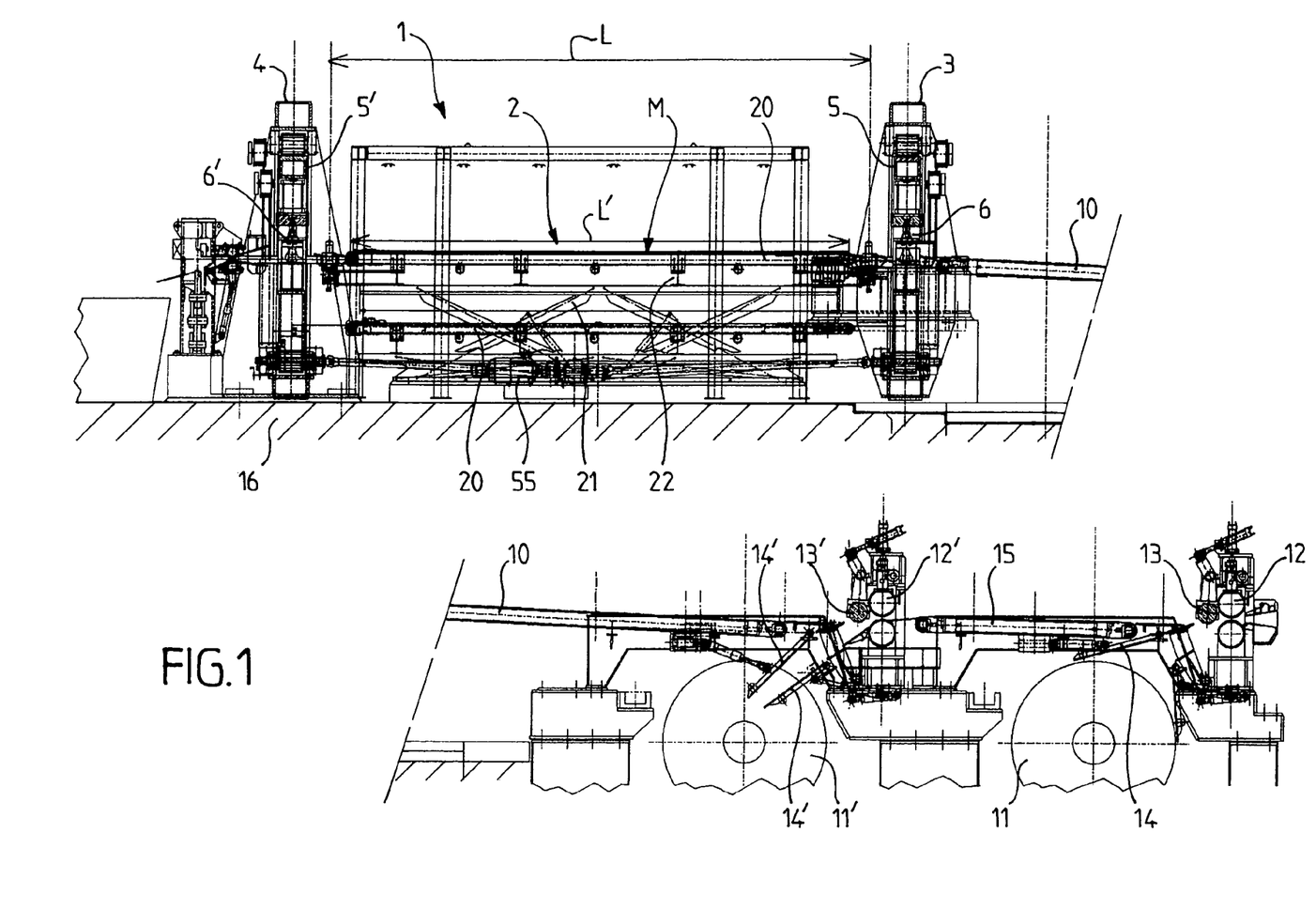
FIG. 1 is a general elevation view, of an inspection device according to the invention, placed at the outlet of a rolling installation.

FIG. 1 represents, as an elevation view, a whole inspection device 1 situated downstream of a continuous treatment installation of a band, for instance a rolling installation. This installation is not represented on the drawing which only shows the outlet including, as usual, two winders 11, 11' operating alternately to enable continuous running of the rolled band.

Each winder 11, 11' is fitted with a pair of pinching rollers 12, 12', a switching roll 13, 13' mobile vertically and a guiding device 14, 14'. Once a coil has been wound, for instance on the first winder 11, flying shears, situated upstream and not represented on the drawing enables to cut the tail of the first band. The latter is wound completely on the winder 11 and the head of the following portion of the band is directed by an intermediate table 15 toward the second winder 11' and deflected toward the chuck thereof by the switching roll 13' and the guiding device 14'. The head of the band then engages on the chuck which is driven into rotation to starting the winding of the following coil.

All these devices are well-known and do not require any detailed descriptions.

Moreover, other devices may be used for winding successive coils without stopping the running of the band, for instance, a carousel-type winder.

To inspect a continuous band as it is running, the flying shears located as seen, upstream of the winding installation, perform two successive cuts as to cut a band sample M of relatively great length, for instance 10 to 15 meters. Preferably, such sampling takes place upon completion of the winding of a coil so that, after evacuating the band sample toward the inspection device, the band may be engaged on the new winder, as indicated above.

After both cuts enabling to isolate a band sample, the latter is directed by the switching members provided on each grip toward the inspection device 1, while passing over a transfer table 10 extending flush with the intermediate table 15, between the second winder 11' and the upstream end of the inspection device 1.

Generally, the inspection device includes two stands, respectively upstream 3 and downstream 4, spaced apart longitudinally by a distance L at least equal to the length of the band sample M and each carrying a rotary platen, respectively upstream 5 and downstream 5', whereon is mounted a clamping grip, respectively upstream 6 and downstream 6'.

Between both stands 3 and 4 is arranged a linking device 2 including a mobile table 20 which, for positioning the band sample M in the inspection device 1, extends flush with the transfer table 10.

Moreover, one of the stands, for instance the downstream stand 4, is fixed whereas the other stand, for instance the upstream stand 3, can be moved longitudinally so as to adjust the distance L between both stands for stretching the band sample as described below.

Figure 2:
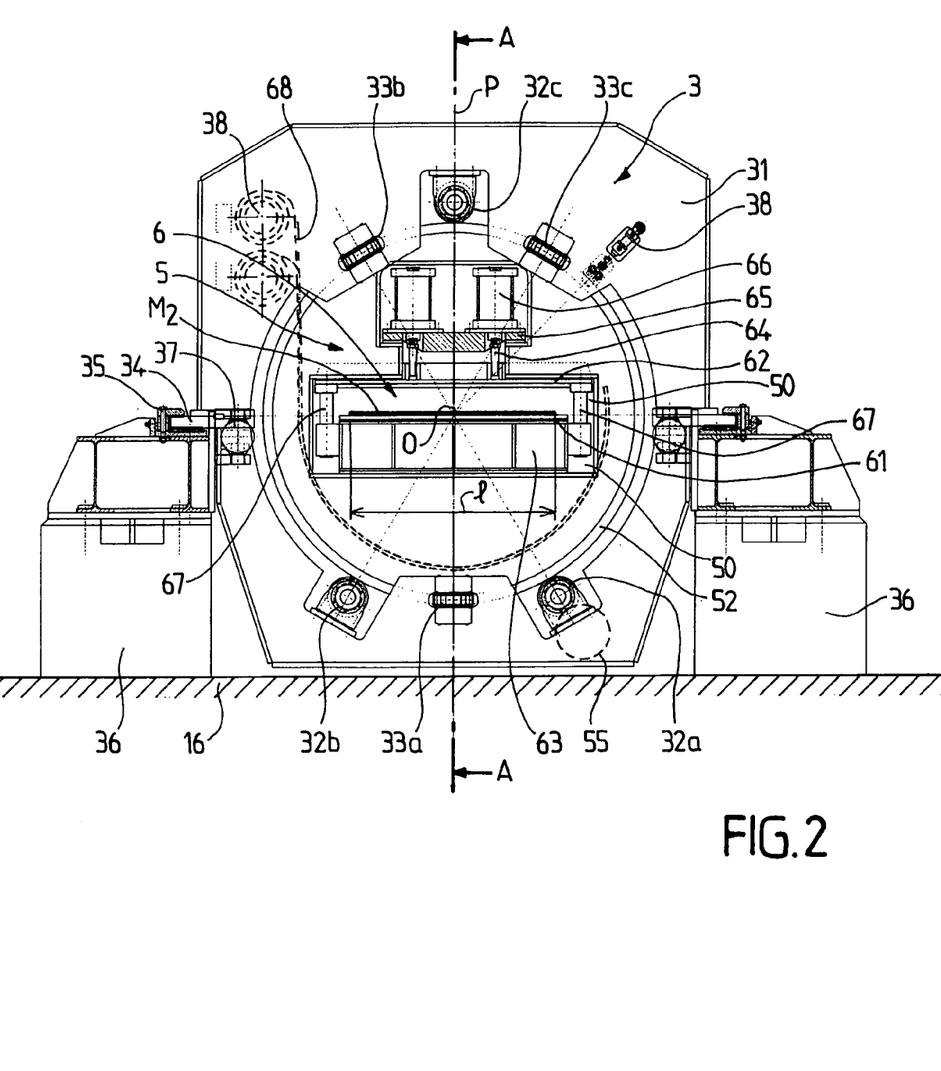
FIG. 2 is a front view of a first clamping grip mounted on a mobile stand.
Figure 3:
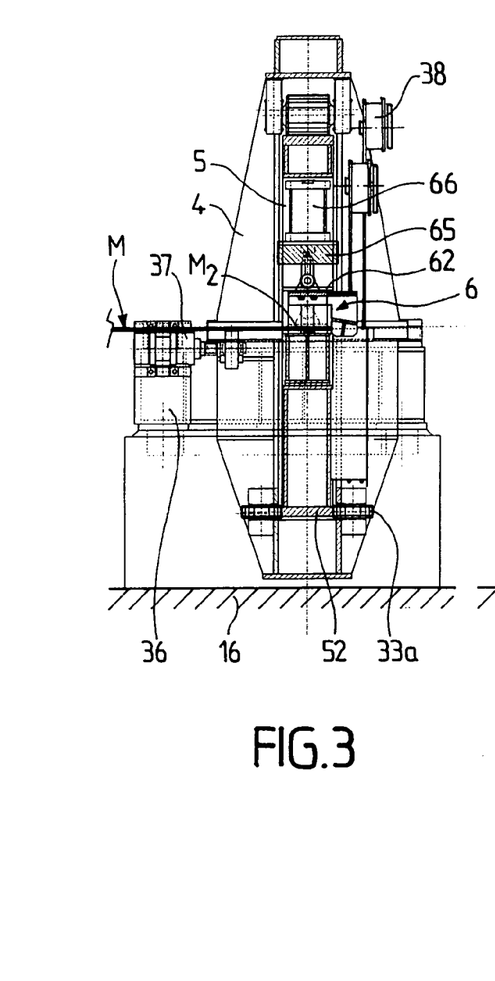
FIG. 3 is a sectional view along line AA of FIG. 2.

FIGS. 2 and 3 show, respectively, as a front view and a sectional view, the upstream stand 3 which is formed, generally, of a rigid frame 31 delineating an opening 30 generally circular in shape, centred on a longitudinal axis O and accommodating the rotary platen 5 carrying the upstream grip 6.

The platen 5, made of mechanically welded construction, includes a chassis in the form of a hollow caisson delineated laterally by two flanges 51 and externally by a circular rim 52 which rests on two lower rollers 32a, 32b spaced apart symmetrically on both sides of a vertical medial plane P of the stand 3 and is held vertically by an upper roller 32c centred in this plane P. The three rollers 32a, 32b, 32c are mounted rotatably on the stand 3 around axes parallel to the longitudinal axis O and arranged so as to centre the circular rim 52 on this axis O.

In addition, the rotary platen 5 is held laterally by three pairs of rollers, respectively lower 33a and upper 33b, 33c, mounted rotatably around concurring axes running through the longitudinal axis O and resting on the lateral sides of the circular rim 52.

At least one of the supporting lower rollers 32a is driven into rotation by a motor 55 so as to control the rotation of the platen 5 around the longitudinal axis O.

The platen 5 carries a clamping grip 6 including two jaws, respectively a fixed lower jaw 61 and a mobile upper jaw 62 with, respectively, two parallel planar clamping faces between them and to the longitudinal axis O.

The lower jaw 61 includes a clamping cheek provided on a beam 63 resting directly on the lower portion of the rotary platen 5. Conversely, the upper jaw 62 includes a clamping cheek formed of a plate connected by articulated rods 64 to a supporting beam 65 which may slide in the platen 5 perpendicular to the clamping face 62, under of the action of two jacks 66, preferably pneumatic.

Guiding rods 67 fixed under the lower face of the jaw 62 and sliding in corresponding housings of the lower beam 63 enable to guarantee the parallelism of the clamping faces 61, 62.

Both clamping faces 61, 62 have a width at least equal to the maximal width I of the band to be inspected 7 and the clamping face of the lower jaw 61 is arranged substantially at the level of the longitudinal axis O.

On the other hand, the rotary platen 5 is fitted, at two jaws 61, 62, with a rectangular scalloping 50 allowing the band to run between both cheeks.

Figure 4:
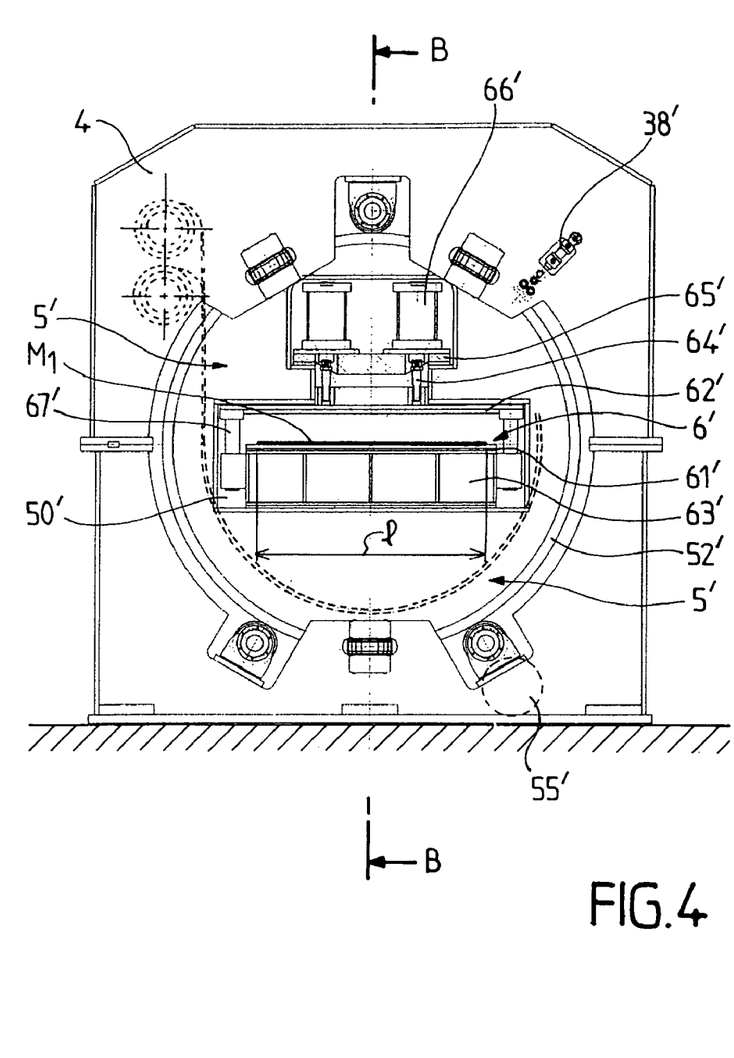
FIG. 4 is a front view of a second clamping grip mounted on a fixed stand.
Figure 5:
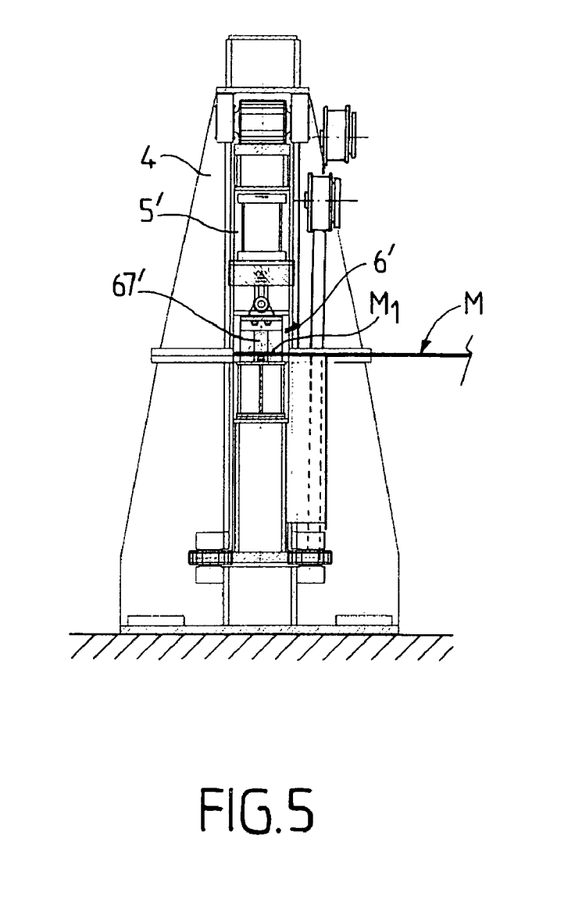
FIG. 5 is a sectional view along line BB of FIG. 4.

As shown on FIGS. 4 and 5, the second clamping grip 6' mounted on the downstream stand 4 is quite similar to the upstream grip 6 which has just been described and includes hence, generally, a fixed jaw 61' situated at the longitudinal axis O and a mobile jaw 62' including a clamping cheek formed of a plate connected by rods 64' to a sliding beam 65' actuated by jacks 66'.

The assembly is carried by a platen 5' mounted rotatably on the downstream stand 4, similarly to the platen 5 on the upstream stand 3.

The same motor 55 or two motors 55 and 55' revolving synchronously, enable to control the simultaneous rotation of both platens 5, 5' around of the longitudinal axis O. Each stand 3, 4 is fitted with a clamping device 38, 38' resting on the rim 52, 52' to lock the corresponding platen 5, 5' in a position for which the clamping faces of both jaws of each grip 6, 6' are parallel to one another and, preferably, horizontal.

As shown on FIGS. 4 and 5, the downstream stand 4 is formed of a rigid frame 41 fixed directly on the foundation block 16.

Conversely, the upstream stand 3 represented on FIGS. 2 and 3, may move parallel to the longitudinal axis O and, to this end, is carried by two side rails 34 sliding in sliding ways 35 mounted respectively on two fixed supporting blocks 36 placed on both sides of the frame 31 of the stand 3. The sliding of the stand 3 is controlled by two jacks 37 resting, respectively, on both supporting blocks 36 and actuated synchronously.

As shown on FIG. 1, between both stands 3 and 4, is placed a linking device 2 including a table 20 which, for placing the band sample M, is situated at the longitudinal axis O of both grips 6, 6', flush with the transfer table 10.

Since the rolled band can be quite slim, the intermediate table 15 leading the band, after shearing, toward the second winder 11', may advantageously be of the magnetic type including a conveyor belt associated with magnets which apply the band onto the belt.

Such an arrangement is known and does not require any detailed descriptions.

Advantageously, the transfer table 10 and the linking table 20 are of the same type so as to enable longitudinal displacement of a slim band, without risking of folding it.

Thus, after cutting, by means of the flying shears, of a band sample M having the desired length, the latter is carried successively by the intermediate table 15 and the transfer table 10 then runs through the upstream stand 3 running through the opening 50 of the platen 5 between the cheeks of the grip 6 which is open. The sample M then lands on the linking belt 20 which carries to the downstream stand 4, so that its front end M1 is situated between the jaws 61', 62' of the downstream grip 6'.

By means of the jacks 37, the mobile stand 3 is position relative to the length of the band sample so that the rear end M2 thereof is situated between the jaws 61, 62 of the upstream grip 6.

Both grips 6, 6' are then clamped on both ends M2, M1 of the band sample and the jacks 37 are actuated so as to push backwards the mobile stand 3 with the platen 5 held by rollers 33, in order to stretch the sample M. Wherein the latter is kept under traction by both grips 6, 6', the linking table 20 may then be lowered in the position 20' represented on FIG. 1. To this end, the magnetic belt 20 can be mounted on a chassis 22 supported by a device of variable height, for instance a shearing system 21.

The conveyor belt 20 which, in its raised position for placing the band sample, lied at the longitudinal axis O, is thus lowered by a distance greater than the maximal value of the semi width l/2 of the band sample M.

Thus, after stretching the band sample M between both grips 6, 6', and lowering the linking table 20, it is possible to inspect first of all the upper face of the sample then to control the simultaneous rotation of both rotary platens 5, 5' around their common axis O to turn the sample M over and inspect its opposite face.

Stretching the band sample M between both grips 6, 6' enables using any inspection system, for instance, by honing, without the sample resting on a support. Consequently, there is no risk of marking the lower face of the sample further to the inspection of the upper face.

After inspection, the table 20 is raised in its upper position. The band sample M may then be released by opening the grips 6, 6' and bears again on the conveyor belt 20 which is then actuated to evacuate downwards the band sample running through the opening 50' of the downstream platen 5'.

Preferably, shears 44 situated at the outlet of the downstream stand 4 enable to slice up the band sample M as waste, as it progresses. But the sample M may also be withdrawn by any other means, for instance a travelling crane.

The jacks 66 for clamping the cheeks are supplied with fluid by ducts 68 winding around winding-unwinding drums 38 mounted on the stand 3 so as to enable rotation, in either direction, of the rotary platen 5.

The inspection device which has just been described enables therefore to inspect both faces of a band sample M without resting on a support and is particularly suited to a continuous on-line rolling installation since it can be placed at the outlet thereof, after the winders, wherein the band sample may, advantageously be sampled at the completion of the winding of a coil or at the beginning of the following coil.

However, such an arrangement, since it enables to inspect both faces of a sample without resting on a support, is still advantageous in the case when, as usual, a coil to be inspected is taken from the production circuit, for instance from the conveyor; in order to lay it on an inspection unwinder in order to check a certain length of band.

An inspection device of the typed described previously can be, indeed, suited such a case, for instance as represented on FIGS. 6 to 10.

Figure 6:
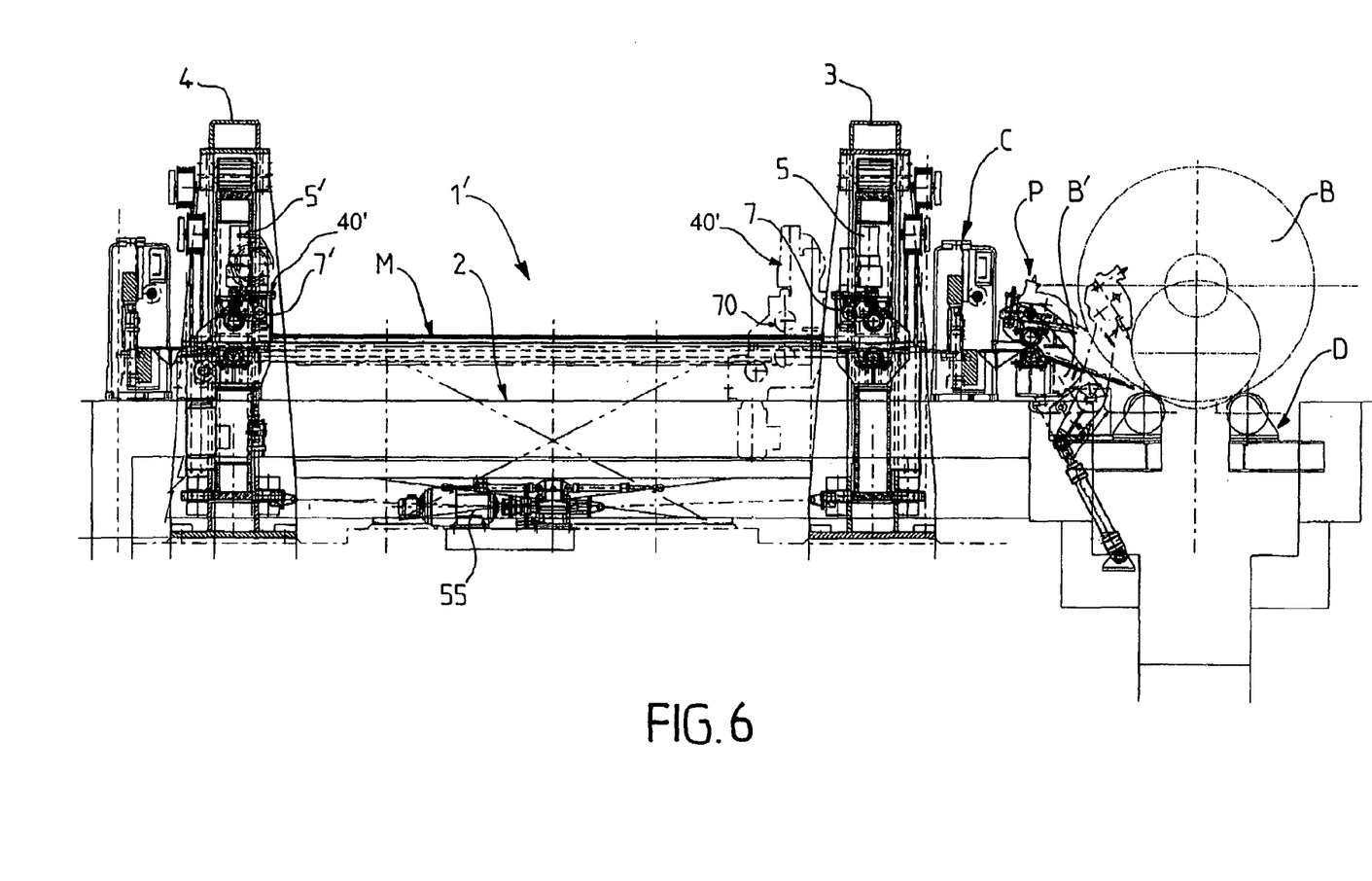
FIG. 6 is a general top view, of another embodiment of the invention.

In such a case, the inspection device 1' still includes two platens 5, 5' each carrying a clamping grip 7, 7' and mounted rotatably, respectively in two stands 3, 4 spaced apart from one another.

However, such device is not arranged, as previously, at the exit of a continuous rolling or processing installation of a band bus simply associated with an inspection unwinder D including, as usual, two spaced apart supporting rolls, whereon can be laid the coil B to be unwound and means not represented for controlling the unwinding. The head B' of the coil may thus be engaged between a pair of pinching rollers P which direct the band toward the inspection device 1' running through shears C situated between the pinching rolls P and the upstream stand 3 of the inspection device 1'.

In the previous arrangement, the drag of the band could be controlled by the intermediate table 15 and the transfer table 10 which, as stated above, are formed advantageously of magnetic conveyor belts. Conversely, in the arrangement according to FIG. 6, only the pinching rolls P are available which cannot feed the band over a great length. To do so, in this new embodiment, the downstream clamping grip 7' is then used, which to this end, is mounted slidingly longitudinally between the downstream rotary platen 5' and the upstream platen 5, so as to be placed immediately behind the upstream grip 7, in the position 70 represented as a mixed line on FIG. 6.

As shown in detail on FIGS. 7 to 10, both clamping grips 7, 7' mounted respectively on the rotary platens 5, 5' are performed similarly to the clamping grips 6, 6' of the device of FIG. 1 and include hence, respectively, a fixed lower jaw 61, 61' provided on a beam 63, 63' resting on the chassis of the platen 5, 5' and an upper jaw 62, 62' provided on an upper beam 65, 65' which is mounted slidingly vertically and actuated by jacks 66, 66'.

However, in this new arrangement, each jaw 61, 62, 61', 62' includes not only a plate forming a clamping cheek, but also, a roll, respectively lower 71, 71' and upper 72, 72', intended for pinching the sheet as described below.

Figure 7:
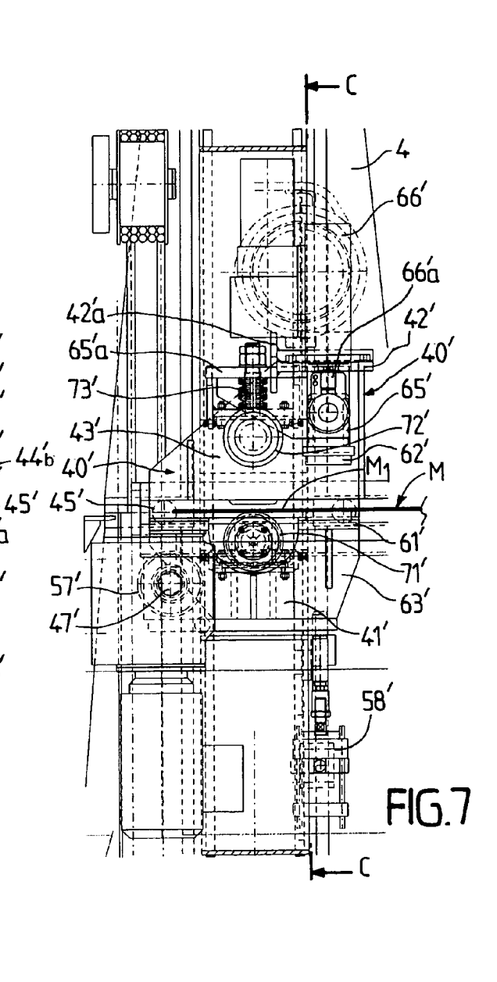
FIG. 7 is a side view of a mobile grip.
Figure 8:
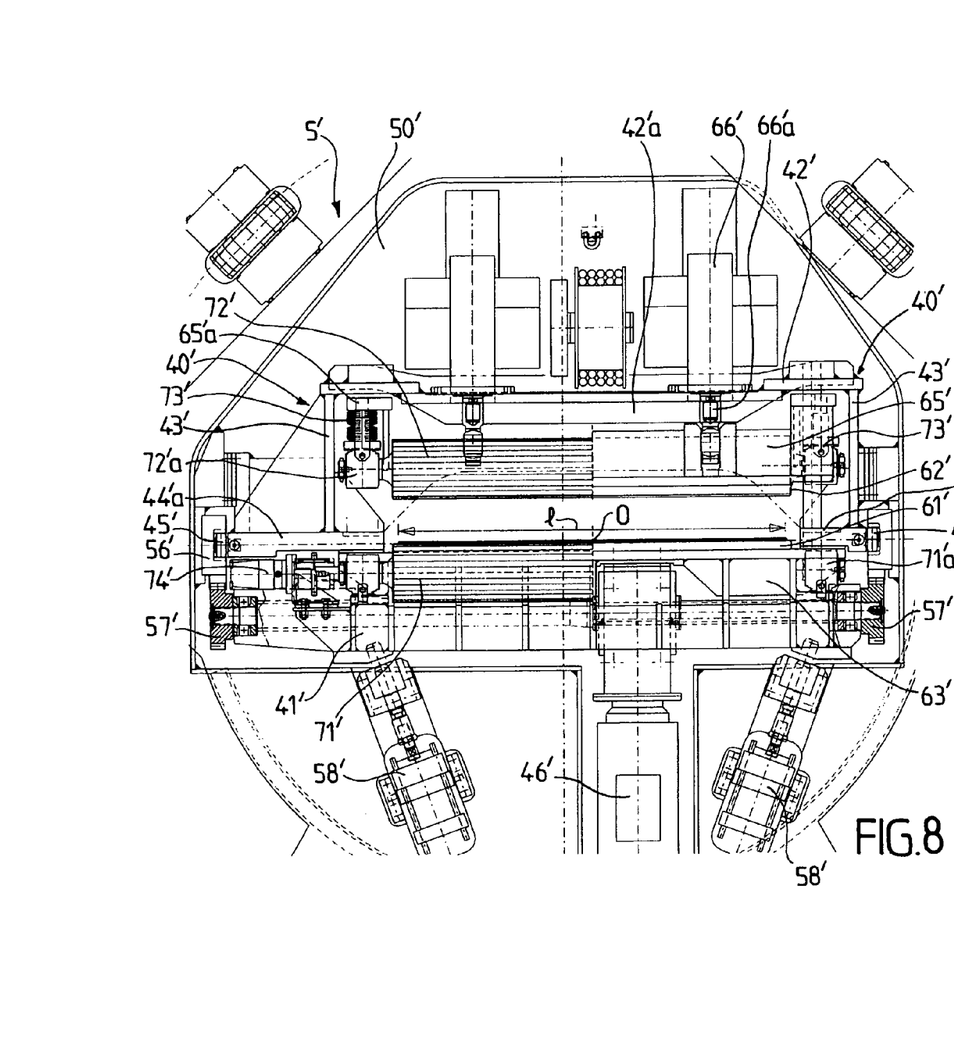
FIG. 8 shows, on the right-hand side, a semi front view of a mobile grip and, on the left-hand side, a semi sectional view along line CC of FIG. 7.

FIGS. 7 and 8 show, in detail, the mobile grip 7' which may move longitudinally and, to this end, is mounted on a carriage 40' in the form of a frame surrounding a central passageway of the sample M, and including two crosspieces, respectively lower 41' and upper 42', connected by side stanchions 43' to two supporting horizontal seats 44'a, 44'b situated substantially at the longitudinal axis O of the device and spaced apart on both sides from the passageway of the band. Each seat 44' carries a pair of guiding rollers 45' sliding respectively in two sections of C-shaped rails 56, parallel to the longitudinal axis O and fastened to the chassis of the platen 5' on the lateral sides of the scalloping 50', on both sides of the longitudinal axis O.

The crosspiece 41' carries, on the other hand, a motor 46' for driving into rotation a transversal shaft 47' revolving on bearings and carrying, at the ends thereof, two pinions 57' each meshing into a rack provided on the lower face of the corresponding rail 56'.

Figure 9:
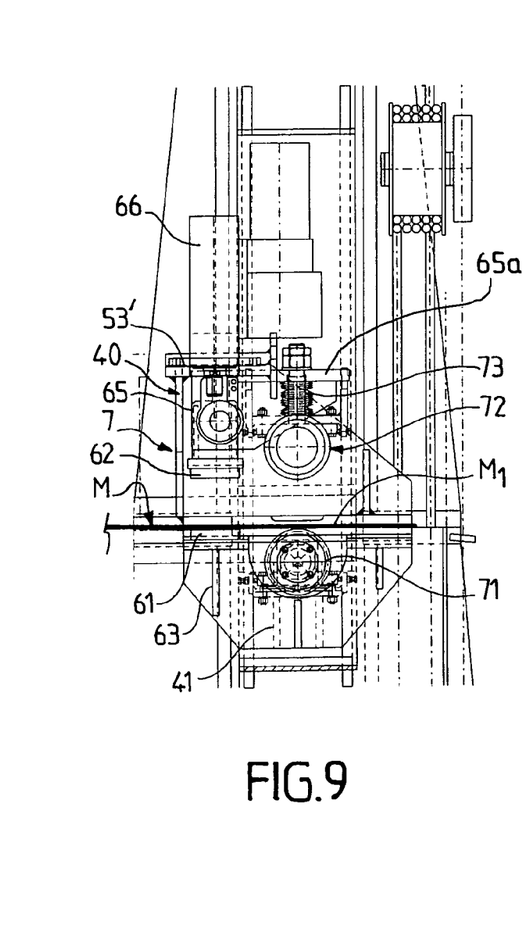
FIG. 9 is a side view of a fixed grip.
Figure 10:
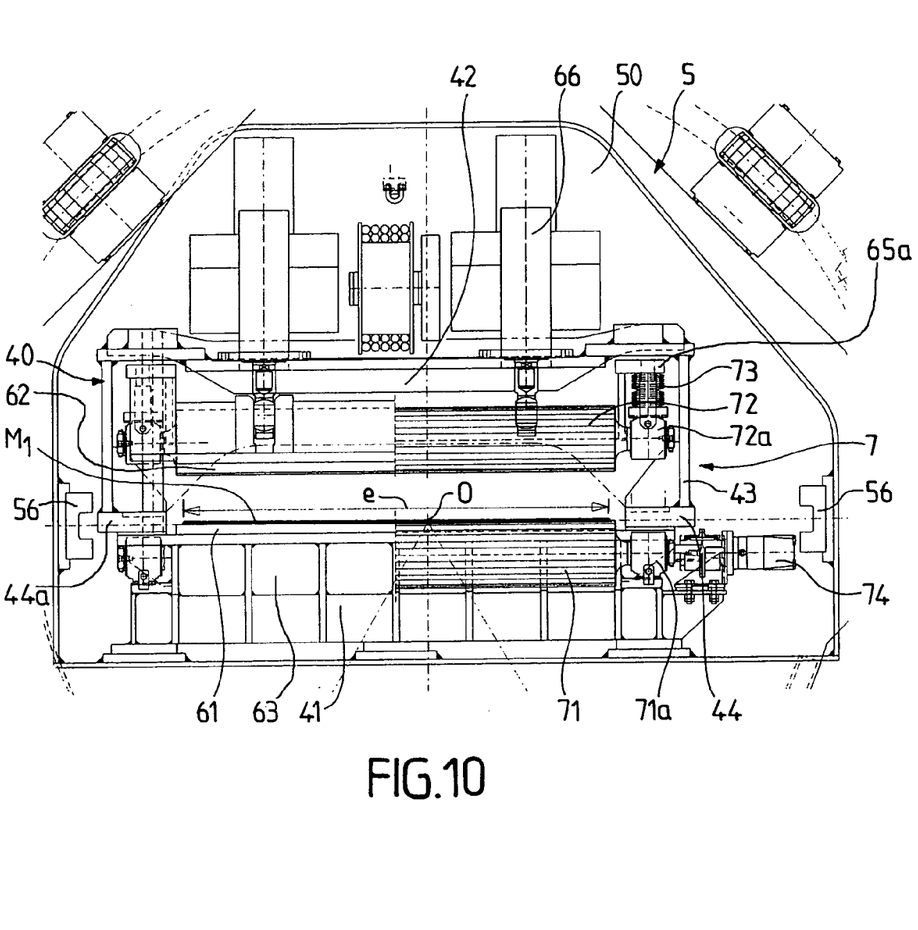
FIG. 10 shows, on the left-hand side a semi front view and on the right-hand side a semi sectional view of the grip along line DD of FIG. 9.

As shown on FIGS. 9 and 10, the upstream grip 7 is mounted similarly in the upstream platen 5, inside a chassis in the form of a frame 40 including a lower crosspiece 41 and an upper crosspiece 42 connected by side stanchions 43 to two horizontal seats 44a, 44b situated substantially at the longitudinal axis O of the device. However, in such a case, the lower crosspiece 41 of frame 40 is fastened directly on the chassis of the platen 5, to the lower portion of the scalloping 50 wherein is situated the upstream grip 7, the assembly being fixed axially.

The rails 56' of the downstream platen 5' only extend over the length thereof and, similarly, the upstream platen 5 is fitted with sections of rails 56 fastened to the sides of the scalloping 50. Both these pairs of short rails 56, 56' are arranged in the extension of one another and connected by two rails 26 fastened on both sides of the longitudinal axis O on the lateral sides of a linking chassis not represented between both platens 5, 5', so as to leave a free passageway of the carriage 40' for supporting the mobile grip 7'.

Consequently, the motor 46' carried by the carriage 40' may control the longitudinal displacement thereof between the position represented on FIGS. 7 and 8 for which the carriage 40' and the grip 7' are situated inside the downstream platen 5' and a position 70 for picking up the band, represented as a mixed line on FIG. 6 and for which the mobile grip 7' is placed immediately downstream of the fixed grip 7.

Thus, at the beginning of the unwinding of a coil B, the pinching rolls P may feed the head of the band first of all into the shears C for cropping the band by cutting the front end M2 thereof then, successively into the upstream grip 7 and the downstream grip 7' situated in the position 70.

The front end M2 of the band may then be picked up by the grip 7' moving downwards, by unwinding the coil B, up to the turning-over position, inside the downstream platen 5'. The carriage 40' is then interconnected with the platen 5' by two clamping members 58' each including, for instance, a spindle actuated by a jack and engaging into a corresponding orifice of the lower crosspiece 41' of the carriage 40'.

At the end of the unwinding of the band, the shears C have cut the rear end M1 thereof so that such rear end is situated at the rear face of the upstream platen 5 when the carriage 40' arrives with the grip 7' inside the downstream platen 5'.

As previously, the band sample M must be stretched for inspection. To do so, in the embodiment of FIG. 6 with unwinder, each of the grips 7, 7' is fitted with a pair of pinching rollers, respectively 71, 72 and 71', 72'.

As shown on FIG. 7, the lower jaw of the downstream mobile grip 7', includes hence a plate 61' forming a clamping cheek which is followed, in the running direction, of a roll 71' tangent to the clamping plane defined by the upper face of the cheek 61'. Such lower roll 71' is mounted rotatably on bearings 71*a*' resting in the central portion of the lower crosspiece 41' which is U-shaped with a raised rear portion, forming the beam 63' for supporting the lower cheek 61' situated then slightly behind the roll 71'.

Similarly the upper jaw of the mobile grip 7' includes a plate forming a upper cheek 62' followed, in the running direction of a roll 72'.

The upper cheek 62' is placed vertical to the lower cheek 61' on an upper beam 65', which is mounted slidingly vertically between both stanchions 43' of the carriage in the form of a frame 40', below the upper crosspiece 42'. The latter can be formed of a simple seat reinforced by a gusset 42'*a* and whereon are fastened the bodies of the clamping jacks 66' whereof the stems 66'*a* are hinged on the beam 65'. As shown on FIG. 7, both clamping cheeks 61', 62' are centred on a single vertical plane running through the axes of both jacks 66'.

The beam 65' for supporting the upper cheek 62' is fitted, at the ends thereof, with two supporting portions 65'*a* protruding forwards and form each a suspension seat of an end of the upper roll 72' which is centred in the vertical plane running through the axis of the lower roll 71'.

This upper roll 72' is indeed carried by two bearings 72'*a* whereof the retainer rings are hanging from two protruding portions 65'*a*, each by a stem 73' whereon is threaded a spring formed, for instance, of a stack of Belleville washers resting, downwards on the retainer ring of the bearing 72'*a* and upwards on the protruding portion 65'*a* of the beam 65'.

The lower roll 71' is arranged on the crosspiece 41' of the carriage 40' so that its upper back-up generatrix is situated at the same level as the clamping face of the lower cheek 61'. Conversely, in the spaced apart position of the cheeks represented on FIG. 7, the back-up generatrix of the upper roll 72' is situated slightly below the level of the clamping face of the upper cheek 62'.

Consequently, when the clamping jacks 66' are actuated for picking up the front end M1 of the band, in the position 70 of the mobile grip 7', the upper roll 72' touches the band M before the upper cheek 62' and exerts hence on the sheet metal a clamping pressure determined by crushing the springs of both suspension members 73'. These springs may be calibrated so that such clamping pressure is sufficient, first of all for driving the band with the grip 7' when the carriage 40' is brought back into the downstream platen 5' then, after cutting the sample M, for stretching said sample before clamping the cheeks.

Indeed, as stated above, the rear end M1 of the band sample M has been cut by the shears C and is situated between both jaws of the fixed grip 7 arranged in the upstream platen 5.

As shown on FIGS. 9 and 10, this fixed grip 7 is realised similarly to the mobile grip 7'. Each jaw of the fixed grip 7 includes hence a seat forming a clamping cheek and associated with a roll but, in such a case, both rolls 71, 72 are situated upstream of two clamping cheeks 61, 62.

Same as for the mobile grip, the lower roll 71 of the fixed grip 7 is carried by bearings 71*a* placed n the central portion of the lower crosspiece 41 which is U-shaped. In such a case, however, it is the front portion, in the running direction, of this crosspiece 41 forming the lower beam 63 for supporting the lower cheek 61 and the latter is centred in the same vertical plane as the upper cheek 62 carried by the upper beam 65 which is mounted slidingly between two side stanchions 43 connected by an upper crosspiece 65 whereon rest the bodies of the clamping jacks 66 whereof the stems are hinged on said upper beam 65. The latter is fitted, at the ends thereof, with two portions 65*a* protruding backwards, above the ends of the upper roll 72 which is centred in the same vertical plane as the lower roll 71, i.e. upstream of both clamping cheeks 61, 62. Such upper roll 72 is centred on two bearings 72*a* hanging from both protruding portions 65*a* of the beam 65, each by a suspension rod 73 whereon is threaded a spring 73*a* which is compressed between the retainer ring of the bearing 72*a* and a seat forming the upper portion of the protruding portion 65*a*

Same as for the mobile grip 7', the springs are calibrated so that the lower back-up generatrix of the upper roll 72 is situated a little below the clamping face of the upper cheek 62 in the spaced apart position of the cheeks represented on FIGS. 9 and 10.

The device then operates as follows.

As stated above, after shearing the front end M1 of the band, the latter is picked up by clamping between both rolls 71', 72' but the clamping pressure is exerted only by the calibrated springs 73', without any contact of the clamping cheeks 61', 62'. Such pressure is however sufficient to enable the unwinding of the band by moving the carriage 40' which is guided successively by the rails 56 of the upstream platen 5 and the intermediate rails 26, before engaging into the rails 56' of the downstream platen 5'. Once unwound completely, the band has been shorn by the shears C so as to provide the rear end M2 of the band sample M which is now placed in the fixed grip 7 when the mobile grip 7' has come back into the downstream platen 5', the assembly being interconnected longitudinally by the clamping members 58'.

The jacks 66 of the fixed grip 7 are then actuated so as to clamp the rolls 71, 72 on the upstream end M1 of the band sample M but, same as for the mobile grip 7', the displacement of the upper cheek 62 is stopped before touching the sample M. The latter is hence held solely between both pairs of rolls 71, 72 and 71', 72' and the pressure resulting from the calibration of the springs 73*a*, 73'*a* is adjusted so as to enable the stretching of the band by rotation in reverse direction of the lower rolls 71, 71' driven each by a motor 74, 74'.

The band thus being stretched, the jacks 66, 66' of each of the grips 7, 7' may be actuated again to clamp each end M1, M2 of the sample between the cheeks, respectively 61, 62, 61', 62', of both grips 7, 7'.

The tensile load applied to the sample by the rotation in reverse direction of both pairs of rolls must be sufficient to enable inspection by honing of the sample without the latter being applied onto a table. Since, after stretching, the sample is clamped, at the ends thereof, between both pairs of cheeks 61, 62, 61', 62', such tensile load can be held for inspection of a first face then, after turning over by simultaneous rotation of both platens 5, 5', for inspection of the second face.

In this embodiment, it is not necessary to arrange a linking table between both platens 5, 5' since the unwinding of the band is controlled by the displacement of the carriage 40' for supporting the mobile grip, wherein the band may be stretched sufficiently, either by means of the pinching rolls P, or, simply, by braking the unwinder, which enables to open the pinching rolls and, thus, to avoid any risk of contact of both faces of the band sample with another member.

It may, however, be useful to place still a linking table mobile vertically between both platens 5, 5', such table being raised, after inspection, up to the running plane to lay the band sample thereon and facilitate the disposal thereof.

Obviously, the invention is not limited to the details of the embodiments which have just been described by way of example but covers conversely all the variations within the protection framework as claimed, It should be noted, for instance, that before stretching the sample, the motorised pinching rolls of one of the grips might be used for accurate positioning of the sample, the other grip remaining open.

Moreover, to simplify the embodiment with inspection unwinder described above, it would be possible to equip with pinching rolls solely one of both grips which, in such a case, would be used solely for stretching the sample, the latter being held, at the other end by the cheeks of the other grip.

On the other hand, other equivalent means could be used for clamping the ends of the sample, stretching and turning the latter over.

The invention claimed is:

1. A method of inspection of a rolled band, wherein a band sample (M) is inspected on a first face and then turned over for the inspection of a second face, said band sample (M) having a substantially rectangular shape centred on a longitudinal axis O, with two transversal ends spaced apart from one another by the length of the band sample, characterised in that, by running parallel to its longitudinal axis, the band sample (M) is brought between two spaced apart grips (6, 6') (7, 7') which are clamped respectively on each transversal end (M1, M2) of the sample (M), the two grips (6, 6') (7, 7') are spaced apart longitudinally from one another so as to stretch the sample (M) for visual inspection of a first face, then the sample is turned over by simultaneous rotation the two grips (6, 6') (7, 7') around the longitudinal axis O, while holding the tension applied, so as to proceed to the inspection of the second face.

2. A method of inspection according to claim 1, characterised in that, by running longitudinally, the band sample (M) is first laid on a table (20) situated between two spaced apart grips (6, 6'), in that the grips (6, 6') are clamped respectively on the two ends (M1, M2) of the sample (M) and then spaced apart longitudinally from one another so as to stretch the sample (M), in that the table (20) is then withdrawn and the inspection is carried out first of all on a first face and then, after turning over, on the second face of the sample (M).

3. A method of inspection according to claim 1, of a band wound into a coil and placed on an inspection unwinder (D) associated with means for controlling the unwinding of the band along a longitudinal direction and shearing means (C), characterised in that the unwound band is first shorn to provide a band sample (M) with a front end ($M_1$) running successively between two open grips, respectively a first grip (7) carried by a rotary platen (5) centred on a longitudinal unwinding axis (O) and a second grip (7') carried by a carriage (40') mounted slidingly longitudinally and situated downstream of the first grip (7), then the second grip (7') is clamped on said front end ($M_1$) and the carriage (40') is moved longitudinally downwards to control the unwinding of the band and to be fastened, with said second grip (7'), on a second rotary platen (5') spaced apart longitudinally from the first platen (5) and centred on a longitudinal axis (O), the band is then shorn to provide a rear end ($M_2$) of the band sample, on which the first grip (7) is clamped, and the sample (M) is stretched between the two grips (7, 7') so as to be inspected successively on a first face and then on a second face after turning over by simultaneous rotation of the two platens (5, 5') around their axis, while holding the tension applied.

4. A method according to claim 3, characterised in that the clamping of at least one end of the band sample (M) in at least one of the grips (7, 7') is conducted by gripping between two rolls (71, 72) (71', 72') and at least one (71) (72) of said rolls is driven into rotation, for stretching the band (M) before clamping it between two cheeks of the grip (7, 7').

5. A method of inspection of a band sample (M) according to any one of the claims 1 to 4, wherein the inspection is conducted by honing, i.e. by rubbing a stone over the face of the sample to make the defects visible, characterised in that, by spacing apart longitudinally the two clamping grips (7, 7'), the band sample (M) is stretched sufficiently so as to conduct the honing on each of its two faces without application of the opposite face onto a table.

6. An inspection device for a rolled band comprising means for sampling, on the rolled band, a band sample (M) of substantially rectangular shape with a longitudinal axis and two transversal ends (M1, M2) spaced apart by the length of the sample (M), means for holding the sample along a plane for the visual inspection of a first face, and means for turning the sample over for inspection of a second face, characterised in that it includes two spaced apart clamping grips (6, 6') (7, 7') for clamping respectively the two transversal ends (M1, M2) of the sample (M), the grips being carried respectively by two platens (5, 5') mounted rotatably around the same longitudinal axis, each in a supporting stand (3, 4), means (37) for stretching the sample (M) by spacing apart the two grips (6, 6') (7, 7') after clamping the ends (M1, M2) of the sample (M) for holding it along an inspection plane running through the longitudinal axis (O), and means (55, 55') for controlling the simultaneous rotation, around the longitudinal axis O, of the two platens (5, 5') with the grips (6, 6') for turning the sample (M) over while holding the tension applied thereto between both grips (6, 6') (7, 7').

7. An inspection device according to claim 6, characterised in that each rotary platen (5, 5') includes a chassis in the form of a circular disk centred on the rotational longitudinal axis (O) and fitted with a central scalloping (50, 50') wherein is mounted a grip (6, 6') including two clamping jaws (61, 62) (61', 62') movable relative to one another, perpendicular to the rotational longitudinal axis (O), and means (66, 66') for controlling the clamping and the releasing of said jaws (61, 62) (61', 62') resting, in opposite directions, on the chassis of the platen (5, 5').

8. An inspection device according to claim 7, characterised in that the two rotary platens (5, 5') are mounted respectively in two supporting stands (3, 4) in the form of a frame spaced apart from one another and that each platen (5, 5') is delineated by a circular rim (52, 52') and rests on a pair of two rollers spaced apart symmetrically on the two sides of a medial vertical plane and mounted rotatably on the stand (3, 4) around axes parallel to the rotational longitudinal axis, the device including, moreover, synchronised means (55, 55') for driving into rotation, around their axis, at least one roller (32, 32') supporting each of the two platens (5, 5'), for turning over the sample clamped between the jaws (61, 62) (61', 62') of both grips (6, 6'), by the simultaneous rotation of both circular platens (5, 5').

9. An inspection device according to claim 8, characterised in that each supporting stand (3, 4) carries at least two pairs of holding rollers (33) mounted rotatably around axes running through the rotational longitudinal axis of the platen and resting on the lateral sides of the rim (52, 52'), on both sides thereof, for centring the platen (5, 5') on a plane perpendicular to the rotational longitudinal axis (O).

10. An inspection device according to any one of the claims 6 to 9, characterised in that each clamping grip (6, 6') includes two jaws, respectively a fixed jaw providing a planar clamping face (61) situated substantially on the rotational axis (O) and a mobile jaw (62) providing a planar clamping face parallel to the clamping face of the fixed jaw (61) and including a beam (65) mounted slidingly perpendicular to said planar faces and a means (66) for moving the mobile jaw (62) relative to the fixed jaw (61) for clamping and releasing said planar faces.

11. An inspection device according to any one of the claims 6 to 9, characterised in that one of the platens (5) is carried by a fixed stand (4) and that the other platen (5') is carried by a mobile stand (3) mounted slidingly on a fixed support (36), parallel to the rotational longitudinal axis of both platens, said fixed stand (36) carrying means (37) for controlling the sliding of the mobile stand (3) for stretching the band sample (M) after clamping the grips (6, 6').

12. An inspection device according to any one of the claims 6 to 9, characterised in that it includes a table (20) mobile vertically, extending between the two rotary platens (5, 5') and having a planar upper face parallel to the rotational longitudinal axis, and means (21) for the vertical displacement of the table (20) between a raised position where its upper face lies substantially at the clamping grips (6, 6') and a lowered position.

13. An inspection device according to claim 11, characterised in that it includes means (15, 10, 20) for conveying the band sample (M) between the grips (6, 6'), which are arranged so as to determine, after cutting the band sample (M), a continuous displacement of the band sample parallel to itself, up to an inspection between both rotary platens (5, 5').

14. An inspection device according to claim 13, characterised in that the conveying means of the band sample (M) include a supporting table (20) having a planar upper face extending, in a pick-up position by the grips (6, 6'), in a clamping plane running through the rotational axis (O) of both platens (5, 5') and means (12, 15, 10) for moving the band sample (M), parallel to itself, from the shears (C) to the supporting table (20).

15. An inspection device according to claim 14, characterised in that it includes means (21) for controlling the vertical displacement of the supporting table (20), parallel to itself, between a first laying and pick-up position of the band sample (M) by the grips (6, 6') and a second turning-over position of the sample (M), the table being then spaced apart.

16. An inspection device according to claim 13, characterised in that the conveying means of the band sample (M) include a transfer table (10) having an upstream end, in the displacement direction, extending above a device (11, 11') for winding the rolled band into a coil and a downstream end situated at the supporting table (20).

17. An inspection device according to claim 13, characterised in that the installation includes, downstream of the shears, switching means (14, 14') having two positions, respectively a first position for guiding the band towards means (11, 11') for winding the band into a coil and a second guiding position for guiding, towards the inspection device (1), a band sample (M) taken from the band by successive shearing of two ends (M1, M2) spaced apart with the required distance.

18. An inspection device according to any of the claims 6 to 9, of a band wound into a coil, characterised in that it includes an unwinder (D) whereon the coil (B) to be inspected is laid, means for controlling the unwinding of the band along a longitudinal running direction, means (C) for shearing the band along a line transversal to the unwinding direction and two grips (7, 7') for clamping the band situated after one another along the longitudinal unwinding direction, respectively a first grip (7) carried by a first platen (5) situated downstream of the shearing means (C), in the unwinding direction and a second grip (7') carried by a carriage (40') mounted slidingly, parallel to the longitudinal unwinding direction, between a first laying and pick-up position of the band, situated immediately downstream of the first grip (7), and an inspection position for which the carriage (40') for supporting the second grip (7') is fastened to a second rotary platen (5'), spaced apart longitudinally downwards relative to the first rotary platen (5), and centred on a longitudinal axis (O), means (66, 66') for controlling the clamping of the first (7) and of the second grip (7') on two ends, respectively a front (M1) and a rear end (M2), of a band sample (M) taken from the band by successive shearing of said ends, and means for controlling (55, 55') the simultaneous rotation of both rotary platens (5, 5') around their axis (O) for successive inspection of a first face and a second face of the band sample (M).

19. An inspection device according to claim 18, characterised in that at least one of the grips includes, on the one hand, two clamping cheeks (61, 62) mounted respectively on two supporting beams (63, 65) movable relative to one another between a spaced apart position and a clamping position of the cheeks (61, 62) and two rolls (71, 72) mounted respectively on both supporting beams (63, 65) beside the corresponding cheek (61, 62), at least one of the rolls (72) being offset vertically relative to the corresponding cheek (62), in the spaced apart position of the cheeks, by a resilient means (73*a*), so that the corresponding end of the sample (M) is gripped between said offset roll (72) and that the other roll (71) before the clamping of both cheeks (61, 62), after compressing said resilient means (73*a*).

20. A device according to claim 19, characterised in that each grip 7, 7' includes a fixed cheek (61) mounted on a beam (63) integral with a fixed crosspiece (41) carrying a first cylindrical roll (71) having a contact generatrix situated at the same level that the clamping face of the fixed cheek (61), and a mobile cheek (62) mounted on a mobile beam (65) movable transversally to the running direction between a spaced apart position and a clamping position of the cheeks (62), said beam (65) having a portion (65'*a*) for supporting a second roll (72) by means of a resilient means (73*a*) for pushing the second roll (72) toward the fixed cheek (61) so said second roll exhibits a contact generatrix offset toward the first roll (71) relative to the mobile cheek (62), and in that, by a first displacement of the mobile beam (65) toward the fixed crosspiece (41), the two rolls (71, 72) bear upon one another before the clamping of the cheeks (61, 62), with an application pressure determined by a calibration of the resilient means (73a), a second displacement of the mobile beam (65) defining the clamping of the cheeks (61, 62) by crushing the resilient means (73a).

21. A device according to claim 19, characterised in that at least one of the rolls (72) is driven into rotation after gripping the sample (M) in a stretching direction thereof, before clamping the corresponding cheeks (61, 62).

22. A device according to claim 20, characterised in that at least one of the rolls (72) is driven into rotation after gripping the sample (M) in a stretching direction thereof, before clamping the corresponding cheeks (61, 62).

\* \* \* \* \*